*United States Patent* [19]

Van Gysel et al.

[11] Patent Number: 5,136,052

[45] Date of Patent: Aug. 4, 1992

[54] PROCESS FOR THE MANUFACTURE OF N-PHENYLMALEIMIDE

[75] Inventors: August Van Gysel, Dilbeek; Ivan Vanden Eynde, Keerbergen; Jean-Claude Vanovervelt, Warchin, all of Belgium

[73] Assignee: U C B, S.A., Brussels, Belgium

[21] Appl. No.: 706,996

[22] Filed: May 29, 1991

[30] Foreign Application Priority Data

Jun. 5, 1990 [GB] United Kingdom ............... 9012453

[51] Int. Cl.$^5$ ............... C07D 207/448; C07D 201/16
[52] U.S. Cl. ............................. 548/549; 548/548; 203/14; 203/58
[58] Field of Search ............................. 548/549

[56] References Cited

U.S. PATENT DOCUMENTS 4,111,879  9/1978  Mori et al. ............... 260/326.5 S X

FOREIGN PATENT DOCUMENTS

| 0129125 | 12/1984 | European Pat. Off. . |
| 0165574 | 12/1985 | European Pat. Off. . |
| 0213933 | 3/1987 | European Pat. Off. . |
| 0334497 | 9/1989 | European Pat. Off. . |
| 0372922 | 7/1990 | European Pat. Off. ............ 548/549 |
| 2649743 | 1/1978 | Fed. Rep. of Germany . |
| 2273952 | 11/1987 | Japan ............................ 548/549 |
| 3039858 | 2/1988 | Japan ............................ 548/549 |
| 2043054 | 10/1980 | United Kingdom . |

OTHER PUBLICATIONS

Patent Abstracts of Japan, vol. 9, No. 260 (C-309) (1983), Abstract of JP 60-112758.
Patent Abstracts of Japan, vol. 9, No. 260 (C-309) (1983) Abstract of JP 60-112759.
Patent Abstracts of Japan, vol. 11, No. 262 (C-442) (1987) Abstract of JP 62-63561.

*Primary Examiner*—David B. Springer
*Attorney, Agent, or Firm*—Wenderoth, Lind & Ponack

[57] ABSTRACT

A process for the manufacture of N-phenylmaleimide which comprises reacting maleic anhydride with aniline in a single step at elevated temperature in the presence of a water-immiscible organic solvent capable of forming an azeotrope with water and of p-toluenesulfonic acis as catalyst. According to the invention, N-phenylmaleimide recovery comprises the successive steps of:

(a) treating the reaction mixture in a dilution and filtration zone, in which it is diluted with an additional amount of the solvent, the diluted mixture being filtered at low temperature in order to separate a solid cake containing the catalyst and impurities, and a liquid filtrate consisting of a solution of N-phenylmaleimide in the solvent, (b) distilling this solution of N-phenylmaleimide under reduced pressure so as to successively separate the solvent and substantially pure N-phenylmaleimide, whereas the distillation residue is treated exactly as indicated in (a) above in a dilution and filtration zone in order to recover the N-phenylmaleimide therefrom, the filtrate being recycled for use in step (a) to dilute the reaction mixture produced by a subsequent synthesis.

Furthermore, the filter cakes from steps (a) and (b) are washed with solvent obtained by distillation in step (b) and the resulting wash solvents are recycled for use in the reaction and/or dilution zones.

A high purity N-phenylmaleimide is obtained in an overall yield exceeding 86 mole %; the problem of waste water and pollution is reduced to a minimum.

15 Claims, No Drawings

PROCESS FOR THE MANUFACTURE OF N-PHENYLMALEIMIDE

The present invention relates to a new process for the manufacture of N-phenylmaleimide, wherein maleic anhydride is reacted with aniline in a single step at elevated temperature in the presence of a water-immiscible organic solvent capable of forming an azeotrope with water and of p-toluenesulfonic acid as catalyst.

N-phenylmaleimide is a compound which has many industrial uses, in particular as a comonomer for improving the thermal stability of acrylonitrile-butadiene-styrene resins, better known by the name "ABS".

There are already various methods for the production of N-phenylmaleimide. Of these processes, the one which produces N-phenylmaleimide in two steps, starting from maleic anhydride and aniline, has been the subject of the greatest number of research work in recent years. In this process, maleic anhydride is first reacted with aniline at moderate temperature, to form maleanilic acid in an almost quantitative yield. Then the maleanilic acid, which may or may not be separated from the reaction medium, is subjected to thermal dehydration at elevated temperature in a water-immiscible organic solvent capable of forming an azeotrope with water, such as toluene, xylene, chlorobenzene and in the presence of an acid catalyst, such as for example sulfuric acid, phosphoric acid and the like, the water formed in the course of the reaction being removed by azeotropic distillation.

More recently, a process for preparing N-phenylmaleimide by reaction of maleic anhydride with aniline in a single step at elevated temperature has also been proposed. Here again the reaction is performed in the presence of a water-immiscible inert organic solvent and an acid catalyst; the reaction is performed at the boiling point of the solvent and the water formed, in the course of the reaction, is removed from the reaction mixture in the form of an azeotrope with the solvent (see European patent application No. 129,125).

This single step process is more favorable than the two step process, since the single step process does not require large quantities of solvent, in contrast to the two step process, in which extensive dilution in the solvent is essential in order to maintain the almost insoluble maleanilic acid is suspension in the reaction medium. The single step process therefore can be performed in smaller and less expensive equipment and with less energy consumption.

However, a difficulty to which no known method escapes is that the production of N-phenylmaleimide is accompanied by numerous secondary reactions and inevitably leads to an accumulation of undesirable impurities in the N-phenylmaleimide produced. Indeed, during the course of the reaction, maleanilic acid and maleic acid can be produced from N-phenylmaleimide and maleic anhydride respectively by hydrolysis, since the azeotropic removal of the water is not necessarily instantaneous. Furthermore, the acid catalyst favors isomerization of maleanilic acid into fumaranilic acid and of maleic acid into fumaric acid. Also, since the N-phenylmaleimide obtained at the end of the reaction is thermally unstable, the product readily degrades at high temperature. Furthermore, under the influence of the acid catalyst, maleanilic acid tends to condense with itself, with maleic and/or fumaric acid to form polycondensation products of high molecular weight. Finally, N-phenylmaleimide has a double bond in its molecule and, therefore, may undergo a radical polymerization.

It should be noted that the problem of the secondary reactions and the impurities occurs even more acutely in the single step process than in the two step process, because in the single step process, the starting material is maleic anhydride, which is placed immediately in the presence of the acid catalyst at a high temperature at which partial isomerization of the maleic acid into fumaric acid inevitably occurs. Thus, at first sight, it would appear more difficult to obtain an N-phenylmaleimide of high purity in the single step process than in the two step process.

However that may be, in either case, the problem arises of separating the impurities from the N-phenylmaleimide obtained at the end of the reaction. This operation is delicate and, in addition, inevitably results in more or less important losses of N-phenylmaleimide.

When the literature in this field is studied one is obliged to conclude that all the processes hitherto described for the recovery and purification of N-phenylmaleimide encounter various practical difficulties. In fact, very few of these processes can be taken into account for easy and economic application on an industrial scale.

As an example, U.S. Pat. No. 4,111,879 discloses a process in which, after the reaction, the solvent is distilled off and then the reaction mixture is poured into a large amount of water, the resulting precipitate is separated by filtration and the desired product recrystallized from ethanol.

If this process were to be applied on an industrial scale, it would require a water consumption of 17 liters per kilogram of N-phenylmaleimide produced. The process inevitably results in the production of large amounts of water contaminated with various acid impurities, which would have to be disposed of, giving rise to serious ecological problems.

There are similar recovery techniques, but wherein the product is precipitated from an organic solvent, followed if necessary by recrystallization from another solvent. These processes obviously result in pollution problems similar to those mentioned above, not to mention that in this case there is the additional hazard of fire, intoxication and inevitable solvent losses in the course of their recycling.

In processes which resort to distillation, there are additional losses due to the decomposition of the N-phenylmaleimide and to the formation of polymerization products, which accompany this operation. Indeed, the various acid by-products and the acid used as a catalyst favor the formation of high molecular weight condensation products during distillation at high temperature. These not only constitute a loss of yield, but also involve a risk that the equipment becomes obstructed. In the best situations, losses of N-phenylmaleimide in the course of distillation are about 15% by weight, of which 5 to 10% by weight is in the form of polymers and about 5 to 7% by weight is in the form of product which is irrecoverable from the distillation residue.

U.S. Pat. No. 4,623,734 describes a process for the production of maleimides in two steps, in which it is proposed that the crude maleimides should be purified by washing them with water, followed by distillation in the presence of a stabilizer. In accordance with a preferred embodiment, an organic acid or inorganic acid, for example sulfuric acid in an amount of at least 1% by weight based on the maleanilic acid used as the raw material, is added to the crude maleimides, the resultant mixture is treated at a temperature in the range of 5° to 100° C., a viscous resinous substance, which contains the by-products formed during the synthesis, is separated out and the organic layer so treated is washed with water in an amount of 1 to 5 times (by weight) the amount of maleanilic acid used as the raw material, so as to deprive the organic layer of water-soluble impurities. Maleimides containing substantially no impurities, from which the solvent is removed by distillation, are thus obtained. The N-phenylmaleimide obtained has a very high degree of purity (99.5 to 99.8% by weight) and the yields are in the range of from 70 to 81 mole % based on the maleanilic acid used (examples 30 and 32 to 34). Using this process all the impurities are effectively separated and N-phenylmaleimide of high purity is obtained.

However, a major disadvantage of this process is that it still requires washing with large amounts of water to remove the impurities, which inevitably entails serious technical and economical difficulties, because this water contaminated by toxic products cannot be discharged into the environment and needs the construction of water purification installations, which involves considerable supplementary investment costs. Furthermore, such washings can cause losses of N-phenylmaleimide due to hydrolysis.

In European patent application No. 213,933, purification is achieved in a similar way; the reaction mixture is washed one or several times with water before the solvent is distilled off. However, unlike the process described above, the purity of the N-phenylmaleimide obtained does not exceed 93.6% by weight. Furthermore, if this process were to be used on an industrial scale it would give rise to the same ecological problems as the process described in U.S. Pat. No. 4,623,734.

Finally, European patent application No. 129,125, which relates to the preparation of N-phenylmaleimide in a single step starting from maleic anhydride and aniline, is very little concerned with the purification of the product obtained. In example 15, the reaction mixture is concentrated by evaporation under reduced pressure and then subjected to extraction with water in order to remove the phosphoric acid used as catalyst, after which the N-phenylmaleimide is distilled. The purity of the product obtained is not, however, indicated.

It is clear that if this process were to be applied on an industrial scale, it would give rise to the same ecological problems as those mentioned above, not to mention that the product would not be sufficiently pure because no provision is made for the removal of the water-insoluble impurities, such as fumaric acid, fumaranilic acid and the like.

In conclusion, it appears that up to the present time a process for producing N-phenylmaleimide has not yet been found which can be applied easily and economically on an industrial scale and which enables to remove effectively all impurities from the system, such as for example the acid catalyst and the by-products such as maleic acid, fumaric acid, maleanilic acid, fumaranilic acid, and the polycondensation products of high molecular weight, without having to resort to treatments which give rise to serious ecological problems and which permits, at the same time, to obtain an N-phenylmaleimide product of very high purity in a high yield.

It is an object of the present invention to provide a solution to this problem.

According to the present invention there is provided an improved process for the manufacture of N-phenylmaleimide, which comprises reacting maleic anhydride with aniline in a single step at elevated temperature in the presence of a water-immiscible organic solvent capable of forming an azeotrope with water and of p-toluenesulfonic acid as catalyst, removing the water formed during the reaction in the form of an azeotrope with the said solvent, and recovering the N-phenylmaleimide from the resulting reaction mixture, wherein the N-phenylmaleimide recovery comprises the successive steps of (a) treating the reaction mixture in a dilution and filtration zone, in which it is diluted with an additional amount of the said solvent, the diluted mixture being filtered at a low temperature in order to separate a solid cake containing the whole of the catalyst and impurities, which cake is washed and removed from the system, and a liquid filtrate consisting of a solution of N-phenylmaleimide in said solvent, and (b) distilling the resulting solution of N-phenylmaleimide under reduced pressure so as to successively separate the solvent and N-phenylmaleimide with a purity of at least 99%, which is recovered as the product of the process, whereas the distillation residue is treated as indicated in (a) above in a dilution and filtration zone in order to recover the N-phenylmaleimide therefrom, the filtrate consisting of a solution of N-phenylmaleimide in the solvent being recycled to step (a), and wherein the filter cakes from stages (a) and (b) are washed with solvent obtained by distillation in step (b) and the resulting wash solvents are recycled for use in the reaction and/or dilution zones.

According to the present invention, it has been found that by using p-toluenesulfonic acid as catalyst in the synthesis of N-phenylmaleimide from maleic anhydride and aniline, it is possible to recover and purify N-phenylmaleimide by a simple, reliable and effective process. Indeed, unlike most acid catalysts such as sulfuric acid and phosphoric acid, p-toluenesulfonic acid used as a catalyst according to the present invention is soluble in the reaction medium at the high reaction temperatures used in the N-phenylmaleimide synthesis, and solid and insoluble in the reaction medium at low temperature. Indeed, when in the anhydrous form, the melting point of p-toluenesulfonic acid is 105° C. Accordingly, the p-toluenesulfonic acid used as catalyst can be easily and completely separated from the reaction mixture by simple low temperature filtration, after appropriate dilution of this mixture by the solvent used as the reaction medium.

Furthermore, according to the present invention, we have, surprisingly, discovered that the low temperature filtration allows to remove not only all the acid catalyst, but also most of the by-products, in particular fumaric acid, fumaranilic and maleanilic acid, and the polycondensation products of high molecular weight, in the form of a solid filter cake, and thus allows to obtain a liquid filtrate consisting of a solution of N-phenylmaleimide, which is completely free from the catalyst and from the greater part of the acid by-products, which, therefore, may be directly subjected, without difficulties, to distillation under reduced pressure, without causing additional losses due to decomposition of the N-phenylmaleimide, and without significantly increasing the amount of polymers formed, which would involve a risk of clogging the apparatus and of retaining an important amount of the desired product in the residue of the distillation.

As a result, N-phenylmaleimide of very high purity is recovered in good yield at the end of the distillation operation.

According to the present invention, the production of N-phenylmaleimide is started with its synthesis, which is effected by the reaction of maleic anhydride with aniline, in a single step, in the presence of a water-immiscible organic solvent and p-toluenesulfonic acid as catalyst.

The amount of catalyst added is about 0.5 to about 4% by weight, preferably 1.5 to 2.5% by weight, referred to the amount of maleic anhydride used. The optimum amount of catalyst to be used can easily be determined by a few preliminary tests.

The molar ratio of aniline to maleic anhydride in the process according to the invention is advantageously from 0.90:1 to 1:1, and preferably from 0.94:1 to 0.98:1, because it is preferable to work with a slight excess of maleic anhydride in order to reduce secondary reactions.

The reaction for the synthesis of N-phenylmaleimide is carried out at a temperature of from 110° to 160° C., preferably of from 130° to 150° C.

A water-immiscible organic solvent capable of forming an azeotrope with water, is used as the solvent in the process according to the invention. Thus, the water formed in the course of the reaction can easily be removed by azeotropic distillation as a mixture with the solvent, by conducting the reaction at the boiling point of the reaction mixture. It is desirable that a solvent whose boiling point is not too low should be selected. Preferably, this boiling point should be above about 110° C., in order to avoid the rate of the reaction becoming too slow. On the other hand, the boiling point of the solvent should not be too high, preferably not exceeding 160° C., because secondary reactions become increasingly dominant at high temperatures. Furthermore, the solvent should be a good solvent for the reactants and N-phenylmaleimide, but a poor solvent for the catalyst and the by-products, so that the catalyst and most of the by-products can be removed by cold filtration of the reaction mixture.

Among the solvents suitable for use in the process of the present invention, mention may be made of chlorinated or non-chlorinated aromatic hydrocarbons such as toluene, xylenes, alkyl-benzenes of which the alkyl radicals have 2 to 3 carbon atoms and chlorobenzene, chlorinated or non-chlorinated aliphatic or cycloaliphatic hydrocarbons such as trimethylhexanes, octane, nonane, ethylcyclohexane, tetrachloroethane or petroleum fractions boiling at 120° to 170° C., and mixtures of the aforesaid solvents.

It is advantageous for the reaction to be performed in the presence of conventional polymerization inhibitors, in order to minimize the polymerization of N-phenylmaleimide. Such inhibitors are well known in the art, and include by way of example, phenols such as 2,6-di-tert-butyl-p-cresol, 2-tert-butyl-hydroquinone, 4-methoxyphenol or 4-tert-butylcatechol, alkyl and aryl phosphites such as tributyl phosphite, triphenyl phosphite, and the like. These inhibitors are added in a total concentration of 0.01 to 0.3% by weight, preferably 0.02 to 0.1%, by weight, referred to the weight of maleic anhydride used.

The synthesis of the N-phenylmaleimide in a single step can generally be carried out in the following manner. Maleic anhydride is dissolved in the solvent in an amount of 15 to 40 parts by weight of maleic anhydride per 100 parts by weight of the mixture of maleic anhydride and solvent, and preferably in an amount of 20 to 30 parts by weight of maleic anhydride per 100 parts by weight of the mixture of maleic anhydride and solvent. p-Toluenesulfonic acid is added to this solution as a catalyst in the proportions indicated above and the mixture is heated to the boiling point of the solvent. Aniline is the progressively added to the reaction mixture. Throughout the course of the reaction, the water formed is removed by azeotropic distillation with the organic solvent.

The reaction time, which generally lies between 3 and 5 hours, is determined by measuring the amount of water recovered.

According to the present invention, N-phenylmaleimide is then recovered from the reaction mixture in two successive steps (a) and (b).

The purpose of step (a) of the process according to the invention is to remove the catalyst and the various by-products from the reaction mixture.

For this purpose, the reaction mixture is diluted with the same solvent as used for the aforementioned reaction in an amount representing 5 to 150% and preferably 10 to 130% of the amount of solvent used in the course of synthesis. This dilution is necessary to avoid precipitation of the N-phenylmaleimide which would be prejudicial to the proper functioning of the process. Furthermore, since N-phenylmaleimide is a good solvent for the by-products which are to be removed, dilution makes it possible for these by-products to be separated in larger amounts. The diluted reaction mixture is then passed to a conventional filtration apparatus and filtered at a temperature between about 20° and about 80° C., preferably about 50° C., if appropriate under a nitrogen pressure of 1 to 5 bars. The filter cake, which contains the whole of the acid catalyst, a small amount of N-phenylmaleimide and the greater part of the secondary products of the reaction, essentially fumaranilic and maleanilic acids, fumaric acid and polycondensation products of high molecular weight, is washed with solvent obtained by distillation in step (b) and then removed from the system as a production residue. The filtrate consists of a solution of N-phenylmaleimide in the solvent.

In step (b) of the process according to the invention, the solution of N-phenylmaleimide obtained in step (a) is distilled under reduced pressure in a conventional distillation apparatus. This operation may optionally be performed in the presence of a polymerization inhibitor such as mentioned above. The solvent is distilled off under a pressure of 70 to 150 mbars and at a temperature from 60° to 100° C., and then the N-phenylmaleimide is distilled off under a pressure of 6 to 25 mbars and at a temperature of 160° to 200° C.

The N-phenylmaleimide recovered as the main fraction from this distillation constitutes the product of the present process; its purity is at least 99.5% by weight and its impurities content is virtually zero. Preferably, a head fraction of N-phenylmaleimide is first distilled off and then recycled to the reactor for a subsequent synthesis of N-phenylmaleimide.

In turn, the distillation residue is treated in exactly the same way as the reaction mixture in step (a) to recover the N-phenylmaleimide which it contains, i.e. it is diluted using the same solvent as is used for the reaction, in proportions permitting easy filtration, and the suspension so formed is passed to a conventional filtration apparatus (which may be the same as that used in step (a)) to separate it into a solid filter cake and a liquid filtrate. The cake, which contains impurities which have not been separated out in the filtration in step (a) and a small proportion of products formed in the course of the distillation, mainly polycondensates, is washed, and then removed from the system as a production residue.

The filtrate, which contains recovered N-phenylmaleimide in solution in the solvent, is recycled for use in step (a) to dilute the reaction mixture produced by a subsequent synthesis of N-phenylmaleimide.

According to the invention, total recycling of the solvent used may be achieved. For this purpose, the filter cakes from step (a) and (b) are washed with solvent obtained by distillation in step (b) and the wash solvents are recycled to the reactor, for use as a solvent in a subsequent synthesis of N-phenylmaleimide. However, total or partial recycling of the wash solvents for use in diluting the reaction mixture in step (a) and/or diluting the distillation residue in step (b) or in any other way permitting appropriate recycling of the solvent, may be considered.

The process according to this invention offers numerous advantages:

a) the N-phenylmaleimide obtained by this process has a purity of at least 99.5% by weight, with a fumaric acid content of 0 to 0.1% by weight, a maleic acid and anhydride content of 0.04 to 0.1% by weight and a maleanilic and fumaranilic acid content of 0.1 to 0.2% by weight;

b) the yield of pure N-phenylmaleimide is very high and attains at least 86 mole % based on aniline used;

c) since the N-phenylmaleimide obtained is of very high purity, it remains stable, even without the addition of stabilizers, under normal storage conditions;

d) unlike certain known processes, it is not necessary to resort to washings with large amounts of water or organic solvents, other than that used in the reaction, in order to remove impurities; the problem of waste water and pollution is thus drastically reduced;

e) because of the complete recycling of the solvent in the system, the only production residue consists of the filter cakes, which contain the whole of the catalyst and the impurities; these are easily destroyed by incineration, thus reducing the problem of water pollution to a minimum;

f) it can be performed in conventional equipment of small size;

g) it is simple, reliable and very economical from the point of view of both investment and operating costs.

The examples given below illustrate the invention without limiting its scope.

EXAMPLE 1

1. First cycle of the N-phenylmaleimide synthesis and purification.

1440 g of xylene, 600 g (6.12 moles) of maleic anhydride, 10 g (0.058 mole) of p-toluenesulfonic acid as catalyst, 150 mg of 4-tertbutylcatechol as polymerization inhibitor and 100 g of N-phenylmaleimide were introduced into a 5 liter reactor equipped with mechanical agitation and heating means, as well as with a condenser having a water separator. The mixture was heated with stirring and refluxed, and then 558 g (6 moles) of aniline were introduced over a period of 4 hours, i.e. a deficit of 2 mole % of aniline with respect to the maleic anhydride. The reaction took place at a temperature of 145° C. The water formed by the reaction was distilled off in the form of an azeotrope with xylene until the reaction was complete; it was continuously separated from the xylene, which is recycled to the reactor.

When the reaction was complete, the reaction mixture was diluted with 1800 g of xylene with stirring. The diluted mixture was allowed to cool and when it reached a temperature of about 50° C., it was filtered under nitrogen pressure.

The filtrate, consisting of a solution of N-phenylmaleimide in xylene, was distilled under reduced pressure. Firstly, 3068 g of xylene were distilled off under a pressure of 100 mbars at a temperature of 78° C. Then, a vacuum of 13 mbars was applied and a head fraction of N-phenylmaleimide, representing 93.4 g, was distilled off at a temperature of 166°–170° C. (which were recycled to the reactor for a subsequent synthesis) and finally, a main fraction of 638.2 g of N-phenylmaleimide was distilled off at a temperature of 171°–173° C. There was thus obtained as product of the process, a pure product which had an N-phenylmaleimide content of at least 99.5% by weight.

The filter cake (115.6 g), which contains the catalyst and the impurities (various by-products from secondary reactions, among others), was washed with 1750 g of xylene originating from the above-mentioned distillation, and then discarded and possibly burnt.

The distillation residue was diluted under stirring with xylene, which had been used for washing the filter cake, and then filtered. The filtrate, which contained recovered N-phenylmaleimide, was recycled for use in diluting the reaction mixture coming from a subsequent synthesis, while the filtration cake, which was still impregnated with xylene, weighed 150 g, was washed with 1300 g of xylene originating from the distillation mentioned above, then discarded and burnt. The wash xylene was recycled to the reactor to be used as a solvent in a further synthesis of N-phenylmaleimide.

2. Second cycle of the N-phenylmaleimide synthesis and purification.

The reactor already contained 1269 g of xylene and 93.4 g of the head fraction of N-phenylmaleimide originating from the first synthesis cycle. 171 g of fresh xylene were added to this to compensate the loss of xylene. 600 g (6.12 moles) of maleic anhydride, 10 g (0.058 mole) of p-toluenesulfonic acid and 150 mg of 4-tert-butylcatechol were then added to the reactor. The procedure as carried out in the first synthesis cycle was then repeated. The mixture was refluxed, 558 g (6 moles) of aniline were added and when the reaction was complete, the reaction mixture was diluted under stirring with the balance of the xylene originating from the first synthesis cycle, which reaches 1800 g of xylene. The diluted mixture was filtered and the filtrate distilled, allowing the recovery of 2950 g of xylene, 115.9 g of head fraction of N-phenylmaleimide (which were recycled to the reactor for a third synthesis), and 814.4 g of a main fraction of N-phenylmaleimide. The filter cake was then washed with the distilled xylene recovered above, and then discarded and possibly burnt.

The distillation residue was diluted with the xylene, which had been used to wash the filter cake, the filtrate was recycled for use in diluting the reaction mixture coming from a third synthesis, while the filter cake was washed with the distilled xylene recovered above, and the wash xylene was recycled to the reactor to be used as a solvent for a subsequent cycle of the N-phenylmaleimide synthesis.

3. Third and subsequent cycles of the N-phenylmaleimide synthesis and purification.

Working exactly as described in paragraph 1 above, a further 10 successive cycles of the N-phenylmaleimide synthesis and purification were performed.

The quantities of the reactants, of the recovered and recycled head fraction of N-phenylmaleimide (PMI), of catalyst, of polymerization inhibitor and the amount of pure N-phenylmaleimide recovered as the main fraction are shown for each synthesis cycle in Table I.

TABLE I

| Synthesis cycle | Maleic anhydride (in g) | Aniline (in g) | Recovered head fraction of PMI (in g) | Recycled head fraction of PMI (in g) | Catalyst (in g) | Polymerization inhibitor (in g) | Pure N-phenylmaleimide (in g) |
|---|---|---|---|---|---|---|---|
| 1 | 600 | 558 | 93.4 | 100.0 | 10 | 0.15 | 638.2 |
| 2 | 600 | 558 | 115.9 | 93.4 | 10 | 0.15 | 814.4 |
| 3 | 600 | 558 | 126.7 | 115.9 | 10 | 0.15 | 973.4 |
| 4 | 600 | 558 | 108.2 | 126.7 | 10 | 0.15 | 800.4 |
| 5 | 600 | 558 | 0.0 | 108.2 | 10 | 0.15 | 840.7 |
| 6 | 600 | 558 | 110.7 | 0.0 | 10 | 0.15 | 764.0 |
| 7 | 600 | 558 | 127.8 | 110.7 | 10 | 0.15 | 873.4 |
| 8 | 600 | 558 | 107.7 | 127.8 | 10 | 0.15 | 942.3 |
| 9 | 600 | 558 | 100.0 | 107.7 | 10 | 0.15 | 814.1 |
| 10 | 600 | 558 | 101.5 | 100.0 | 10 | 0.15 | 864.1 |
| 11 | 600 | 558 | 113.1 | 101.5 | 10 | 0.15 | 923.5 |
| 12 | 600 | 558 | 170.1 | 113.1 | 10 | 0.15 | 892.6 |

Thus, after 12 synthesis cycles 10,141.1 g of N-phenylmaleimide were obtained as main fraction. A further 170.1 g of N-phenylmaleimide were recovered in the last head fraction, 107.4 g from the washed xylene, 9.0 g from the distilled xylene and 389.9 g from the filtrate of the distillation residue, giving a total of 10,817.5 g of N-phenylmaleimide. Subtracting the 100 g of N-phenylmaleimide added during the first cycle, the overall yield was 86.1 mole % of N-phenylmaleimide based on aniline used.

The N-phenylmaleimide content of the pure product so obtained was 99.5% by weight; it contained less than 0.1% by weight of fumaric acid, 0.04 to 0.1% by weight of maleic acid and anhydride, 0.1 to 0.2% by weight of maleanilic and fumaranilic acids and less than 0.1% by weight of undefined compounds of high molecular weight.

EXAMPLE 2

Comparative

Preparation and Purification of N-phenylmaleimide without Prior Filtration

In this comparative example, the reaction mixtures was distilled directly, without prior removal by filtration of the catalyst and the acid by-products produced by the secondary reactions.

1440 g of xylene, 600 g (6.12 moles) of maleic anhydride, 10 g (0.058 mole) of p-toluenesulfonic acid as catalyst, 150 mg of 4-tert-butylcatechol as polymerization inhibitor and 100 g of N-phenylmaleimide were introduced into a reactor having a capacity of 5 liters and fitted with heating and mechanical agitation means and with a condenser having a water separator. The mixture was heated with stirring and refluxed and then, 558 g (6 moles) of aniline were added over a period of 4 hours, i.e. a deficit of 2 mole % with respect to the maleic anhydride. The reaction took place at a temperature of 145° C. The water formed in the course of the reaction was distilled off in the form of an azeotrope with xylene until the reaction was complete.

When the reaction was complete, the reaction mixture was distilled under reduced pressure. Xylene (1397 g) was first distilled off at a pressure of 100 mbars and at a temperature of 78° C. A vacuum of 13 mbars was then applied and 109 g of a head fraction of N-phenylmaleimide having a N-phenylmaleimide content of 96.5% by weight was then distilled off at a temperature of 166°–170° C. This head fraction may be used for a further synthesis of N-phenylmaleimide. The main fraction of N-phenylmaleimide was then distilled off. The size of this main fraction has been found in the laboratory to be extremely variable (about 600 g were recovered in this specific example).

A product was obtained, which had an N-phenylmaleimide content of at best 98.55% by weight. This product, of clearly inferior quality to that obtained in example 1, contained 0.7% by weight of fumaric acid, 0.3% by weight of maleic acid and anhydride and 0.3% by weight of fumaranilic acid as the main impurities.

Also a distillation residue, in very varying amounts, remained at the bottom of the distillation apparatus. This residue consisted of a dark mass from which it was impossible to extract any of the N-phenylmaleimide which it contained. According to analysis by gas phase chromatography (GC) and high performance liquid phase chromatography (HPLC), this distillation residue contained 25% by weight of non-recoverable N-phenylmaleimide, 0.6% by weight of maleic acid and anhydride, 1.4% by weight of fumaric acid, 5% by weight of fumaranilic acid and 68% by weight of further residue (polycondensates, polymers and catalyst). Extrapolated to the pilot stage, the process described in example 2 has even led to N-phenylmaleimide yields of almost zero, due to polymerization of the reaction mixture into a mass in the course of distillation.

This comparative example clearly shows that the presence of the catalyst and the acid by-products in the reaction mixture greatly favors the formation of polycondensation products of high molecular weight in the course of the distillation and contributes to obtain a lower N-phenylmaleimide quality.

Indeed, when examples 1 and 2 are compared, it is found that if distillation of the reaction mixture is performed without prior filtration:
  there is substantial loss of useful product and impure N-phenylmaleimide (purity of 98.55% by weight) is recovered with a very variable yield in view of the risks of polymerization in the course of distillation, the residue which forms in the distillation apparatus contains a considerable quantity of polycondensates and, in addition, N-phenylmaleimide which it is no longer possible to extract.

In contrast, the process according to the invention enables easy and almost complete recovery of the N-phenylmaleimide from the reaction mixture, without significant formation of polycondensation products in the course of the distillation. A high purity product, the N-phenylmaleimide content of which is superior or equal to 99.5% by weight and the impurities content of which is virtually zero, is obtained in an overall yield exceeding 86 mole %. Furthermore, the N-phenylmaleimide which is retained in the distillation residue can easily be recovered.

EXAMPLE 3

Effects of the Filtration on the Composition of the N-phenylmaleimide

This example shows the effects of the filtration of the reaction mixture on the composition of the crude (non-distilled) N-phenylmaleimide. For this purpose, the following data, obtained by GC and HPLC analysis, have been collected together in Table II below, where the composition A is the composition of a crude N-phenylmaleimide obtained according to the process of example 1, before its distillation, i.e. after the reaction mixture has been diluted and filtered and the xylene and the head fraction have been distilled off (called hereinafter product A).

B is the composition of a crude N-phenylmaleimide obtained according to the process of example 2, before its distillation, i.e. after the xylene and the head fraction have been distilled off (without filtration of the reaction mixture; called hereinafter product B, not according to the invention).

TABLE II

| Composition of the crude N-phenylmaleimide(as % by weight) | | |
|---|---|---|
| | A (with filtration) | B (comparison) (without filtration) |
| N-phenylmaleimide | 91.9 | 88.6 |
| p-Toluenesulfonic acid | — | 0.9 |
| Fumaric acid | 0.03 | 0.9 |
| Maleic acid and anhydride | 0.36 | 0.82 |
| Fumaranilic and maleanilic acids | 0.32 | 1.3 |
| Polycondensates and polymers | 7.39 | 7.48 |

This table clearly shows that the crude N-phenylmaleimide obtained from the process according to the invention (product A) is much more pure than the crude N-phenylmaleimide which is not obtained from the process according to the invention, i.e. without dilution and filtration (product B). It can be seen in particular that the fumaric, fumaranilic and maleanilic acid content is much higher in product B.

It can also be seen that the crude N-phenylmaleimide obtained from the process in example 2 (product B not according to the invention) contains furthermore an important amount of acid catalyst, whereas the crude N-phenylmaleimide from example 1 according to the invention (product A) is completely free from it.

By way of indication, Table III below shows the composition of the filter cake obtained in example 1 after filtration of the diluted reaction mixture.

TABLE III

| Composition of the dry filter cake in example 1 (% by weight) | |
|---|---|
| N-phenylmaleimide | 3.3 |
| p-Toluenesulfonic acid | 14.8 |
| Fumaric acid | 7.9 |
| Maleic acid and anhydride | 3.2 |
| Fumaranilic and maleanilic acids | 35.9 |
| Polycondensates and polymers | 34.9 |

It can be seen that the filter cake not only retains the catalyst but also most of the by-products, in particular fumaric acid, fumaranilic acid and maleanilic acid and polycondensation products of high molecular weight.

It should be noted that the small quantity of N-phenylmaleimide contained in the cake may be recovered by washing with xylene which has been used for the synthesis and recycled.

EXAMPLE 4

Thermal Stability of the N-phenylmaleimide a) Stability of the crude N-phenylmaleimide before distillation.

In a first test the thermal stability of the crude N-phenylmaleimide obtained from the process of example 1 according to the invention (product A from example 3) was compared with the thermal stability of the crude N-phenylmaleimide obtained from the process of example 2 not according to the invention (product B in example 3). Before the test 100 ppm of hydroquinone monomethyl ether was added to product B, while product A was used as such. Samples of products A and B were held at 120°, 135° and 150° C. and the following findings were noted after one week; the samples of product A browned slightly, their viscosity remained unchanged and no change in composition was detected by high performance liquid phase chromatography (HPLC); on the other hand, a precipitate which was impossible to dissolve appeared in the samples of product B at 120° and 135° C., and the sample of product B held at 150° C. became insoluble in the eluent making it impossible to analyze by HPLC.

In a further stability test performed at the same temperatures of 120°, 135° and 150° C., pure product A was compared with product A to which 1 and 5% by weight respectively of the filter cake, obtained in example 1 after filtration of the diluted reaction mixture, had been added.

After 9 days, it was found that there was no change in the viscosity of the pure product A, whereas the viscosity of the samples containing the filter cake increased progressively with the course of time; the rate of increase was more rapid with higher percentages of added cake and higher temperatures.

It follows from these tests that the crude N-phenylmaleimide obtained by the process according to this invention is remarkably stable, which permits, where necessary, to store the crude product in the liquid state without appreciable loss, for example while awaiting a distillation operation.

On the other hand, the presence of the organic acids resulting from secondary reactions has an adverse effect on the stability of the N-phenylmaleimide causing the formation of polymerization products.

b) Stability of the distilled pure N-phenylmaleimide.

When samples of the pure N-phenylmaleimide obtained according to example 1 were held at a temperature of 90° C., it was found that these samples showed no change in appearance or composition when analyzed by gas phase chromatography (GC) after 13 days. When held at higher temperatures (120°, 150° and 180° C.) slight browning of the samples was observed after 3 days, but no change in composition was detected by HPLC and GC. The pure N-phenylmaleimide obtained according to the invention is therefore remarkably stable, even when polymerization inhibitors are absent. Hence storage without the addition of stabilizers may, if necessary, be considered, which may be an important advantage in certain specific applications.

We claim:

1. A process for the manufacture of N-phenylmaleimide which comprises reacting maleic anhydride with aniline in a single step at elevated temperature in the presence of a water-immiscible organic solvent capable of forming an azeotrope with water and of p-toluenesulfonic acid as catalyst, removing the water formed during the reaction in the form of an azeotrope with the said solvent, and recovering the N-phenylmaleimide from the resulting mixture, wherein the N-phenylmaleimide recovery comprises the successive steps of:
   (a) treating the reaction mixture in a dilution and filtration zone, in which it is diluted with an additional amount of the said solvent, the diluted mixture being filtered at low temperature in order to separate a solid cake containing the whole of the catalyst and impurities, which cake is washed and removed from the system, and a liquid filtrate consisting of a solution of N-phenylmaleimide in said solvent, and
   (b) distilling the resulting solution of N-phenylmaleimide under reduced pressure so as to successively separate the solvent and N-phenylmaleimide with a purity of at least 99% by weight, which is recovered as the product of the process, whereas the distillation residue is treated as indicated in (a) above in a dilution and filtration zone in order to recover the N-phenylmaleimide therefrom, the filtrate consisting of a solution of N-phenylmaleimide in the solvent being recycled to step (a),
and wherein the filter cakes from steps (a) and (b) are washed with solvent obtained by distillation in step (b) and the resulting wash solvents are recycled for use in the reaction and/or dilution zones.

2. A process according to claim 1, wherein the reaction is carried out at a temperature of from 110° to 160° C.

3. A process according to claim 2, wherein the reaction is carried out at a temperature of from 130° to 150° C.

4. A process according to claim 1, wherein the p-toluenesulfonic acid is used in amount of from about 0.5 to about 4% by weight, referred to the amount of maleic anhydride used.

5. A process according to claim 4, wherein the p-toluenesulfonic acid is used in an amount of from 1.5 to 2.5% by weight, referred to the amount of maleic anhydride used.

6. A process according to claim 1, wherein the molar ratio of aniline to maleic anhydride is from 0.90:1 to 1:1.

7. A process according to claim 6, wherein the molar ratio of aniline to maleic anhydride is from 0.94:1 to 0.98:1.

8. A process according to claim 1, wherein said solvent is at least one member selected from the group of chlorinated aromatic hydrocarbons, non-chlorinated aromatic hydrocarbons, chlorinated aliphatic hydrocarbons, non-chlorinated aliphatic hydrocarbons, chlorinated cycloaliphatic hydrocarbons, non-chlorinated cycloaliphatic hydrocarbons and mixtures of the aforesaid solvents.

9. A process according to claim 8; wherein said solvent is xylene.

10. A process according to claim 1, wherein, in step (a), the reaction mixture is diluted with the said solvent in an amount representing 5 to 150% of the amount of solvent used in the course of synthesis.

11. A process according to claim 1, wherein, in step (a), filtration is performed at a temperature between about 20° and about 80° C.

12. A process according to claim 11, wherein, in step (a), filtration is performed at a temperature of about 50° C.

13. A process according to claim 1, wherein, in step (b), the solvent is distilled off under a pressure of 70 to 150 mbars and at a temperature of 60° to 100° C.

14. A process according to claim 1, wherein, in step (b), a head fraction of N-phenylmaleimide is first distilled off and recycled to the N-phenylmaleimide synthesis step.

15. A process according to claim 1, wherein, in step (b), the N-phenylmaleimide is recovered as the main fraction by distillation under a pressure of 6 to 25 mbars and at a temperature of 160° to 200° C.

* * * * *